(12) United States Patent
Bender et al.

(10) Patent No.: US 10,363,332 B2
(45) Date of Patent: *Jul. 30, 2019

(54) AIR IONIZATION SYSTEM

(71) Applicant: IONaer International Arizona, LLC, Glendale, AZ (US)

(72) Inventors: Timothy Mark Bender, Scottsdale, AZ (US); Perry Pauley, Glendale, AZ (US); Brian Keith Roper, Phoenix, AZ (US); Todd Kenneth Roper, Glendale, AZ (US)

(73) Assignee: IONaer International Arizona, LLC, Glendale, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/914,682

(22) Filed: Mar. 7, 2018

(65) Prior Publication Data

US 2018/0193509 A1  Jul. 12, 2018

Related U.S. Application Data

(63) Continuation of application No. 15/913,677, filed on Mar. 6, 2018, which is a continuation of application
(Continued)

(51) Int. Cl.
| | |
|---|---|
| *A61L 9/00* | (2006.01) |
| *A61L 9/22* | (2006.01) |
| *B01D 53/32* | (2006.01) |
| *B01D 46/00* | (2006.01) |
| *B01D 53/86* | (2006.01) |

(Continued)

(52) U.S. Cl.
CPC .............. *A61L 9/00* (2013.01); *A61L 9/22* (2013.01); *B01D 46/0027* (2013.01); *B01D 46/0028* (2013.01); *B01D 46/0038* (2013.01); *B01D 53/323* (2013.01); *B01D 53/8675* (2013.01); *F24F 3/166* (2013.01); *H01T 23/00* (2013.01); *A61L 2209/11* (2013.01); *A61L 2209/13* (2013.01); *A61L 2209/14* (2013.01); *B01D 53/30* (2013.01); *B01D 53/88* (2013.01); *B01D 2255/2073* (2013.01); *B01D 2255/20761* (2013.01); *B01D 2257/106* (2013.01); *B01D 2257/90* (2013.01); *B01D 2258/06* (2013.01);
(Continued)

(58) Field of Classification Search
CPC .............. A61L 9/00; A61L 9/22; B01D 53/32
USPC ........................................................ 422/121
See application file for complete search history.

(56) References Cited

U.S. PATENT DOCUMENTS

| | | |
|---|---|---|
| 6,791,815 B1 | 9/2004 | Graham |
| 8,747,754 B2 | 6/2014 | Abate |

(Continued)

OTHER PUBLICATIONS

USPTO; Non-Final Office Action dated Jun. 30, 2017 in U.S. Appl. No. 15/156,735.
(Continued)

*Primary Examiner* — Kevin Joyner
(74) *Attorney, Agent, or Firm* — Snell & Wilmer L.L.P.

(57) ABSTRACT

Ionization systems configured with a catalyst-bearing sleeve provide improved filtration while keeping ozone levels within acceptable limits. Modular configurations provide for serviceability and replaceability. System controls monitor particulates, temperature, humidity, and other relevant factors and adjust an ionization level accordingly for optimal performance.

22 Claims, 14 Drawing Sheets

Related U.S. Application Data

No. 15/156,735, filed on May 17, 2016, now Pat. No. 9,907,874.

(51) Int. Cl.
  *F24F 3/16* (2006.01)
  *H01T 23/00* (2006.01)
  *B01D 53/30* (2006.01)
  *B01D 53/88* (2006.01)

(52) U.S. Cl.
  CPC . *F24F 2003/165* (2013.01); *F24F 2003/1682* (2013.01)

(56) References Cited

U.S. PATENT DOCUMENTS

| | | | |
|---|---|---|---|
| 9,907,874 B2 | 3/2018 | Bender et al. | |
| 9,908,081 B2 | 3/2018 | Bender et al. | |
| 9,908,082 B2 | 3/2018 | Bender et al. | |
| 2001/0031234 A1 | 10/2001 | Christodoulatos et al. | |
| 2003/0106788 A1 | 6/2003 | Babko-Malyi | |
| 2004/0007000 A1 | 1/2004 | Takeda et al. | |
| 2008/0035472 A1 | 2/2008 | Lepage | |
| 2008/0063577 A1 | 3/2008 | Crowe | |
| 2008/0317802 A1* | 12/2008 | Lee | A01N 43/80 424/409 |
| 2009/0202397 A1* | 8/2009 | Parker | B01D 53/8675 422/121 |
| 2015/0017059 A1 | 1/2015 | Arlemark | |
| 2015/0076082 A1 | 3/2015 | Loucaides | |
| 2016/0263263 A1 | 9/2016 | Robert | |
| 2017/0189846 A1 | 7/2017 | Cho et al. | |
| 2017/0333587 A1 | 11/2017 | Bender | |
| 2017/0333837 A1 | 11/2017 | Bender | |
| 2017/0333838 A1 | 11/2017 | Bender | |
| 2017/0348636 A1 | 12/2017 | Bender | |
| 2018/0036677 A1 | 2/2018 | Bender | |
| 2018/0193508 A1 | 7/2018 | Bender | |
| 2018/0193794 A1 | 7/2018 | Bender | |

OTHER PUBLICATIONS

USPTO; Non-Final Office Action dated Jun. 30, 2017 in U.S. Appl. No. 15/156,755.

USPTO; Non-Final Office Action dated Jul. 24, 2017 in U.S. Appl. No. 15/156,771.

USPTO; Notice of Allowance dated Dec. 7, 2017 in U.S. Appl. No. 15/156,755.

USPTO; Notice of Allowance dated Dec. 7, 2017 in U.S. Appl. No. 15/156,771.

USPTO; Notice of Allowance dated Dec. 20, 2017 in U.S. Appl. No. 15/156,735.

USPTO; Non-Final Office Action dated Nov. 28, 2018 in U.S. Appl. No. 15/622,027.

USPTO; Non-Final Office Action dated Nov. 28, 2018 in U.S. Appl. No. 15/622,025.

USPTO; Non-Final Office Action dated Dec. 3, 2018 in U.S. Appl. No. 15/913,677.

USPTO; Non-Final Office Action dated Dec. 3, 2018 in U.S. Appl. No. 15/913,733.

\* cited by examiner

AIR IONIZATION SYSTEM

CROSS-REFERENCE TO RELATED APPLICATIONS

This application is a continuation of U.S. Ser. No. 15/913,677 filed on Mar. 6, 2018 and entitled "AIR IONIZATION SYSTEMS AND METHODS". U.S. Ser. No. 15/913,677 is a continuation of U.S. Ser. No. 15/156,735 filed on May 17, 2016, now U.S. Pat. No. 9,907,874 entitled "AIR IONIZATION SYSTEMS AND METHODS". Each of the foregoing applications is incorporated herein by reference in its entirety.

TECHNICAL FIELD

The present disclosure relates to air purification, and in particular to removal of particulates via ionization.

SUMMARY OF THE INVENTION

Disclosed is an air ionization unit that includes an ozone dampening catalyst surrounding the air ionization tube. The ozone dampening catalyst removes much or all of the ozone created by ionizing molecules in the air. In one embodiment, rather than the air passing by the ionization tube and being ionized in a known manner, air is drawn into an ionization module through a filter that may be contained in the module. The filtered air is then expelled, preferably by a fan, outward into a space between the ionization tube and the ozone dampening catalyst. The air is ionized in a standard manner, and ozone is partially or totally removed by the ozone absorption tube.

The air ionization unit may be an integral, one-piece unit, so it can be removed and replaced without having to disassemble it. In a preferred embodiment, the air ionization unit has a support plate that mounts directly or indirectly to the outside surface of an air passageway duct or other space (collectively, "duct") that includes air to be cleaned. The air ionization tube and ozone dampening catalyst preferably extend outward from the support plate and into the air duct. Fasteners on the outside of the air duct can be removed to remove and/or replace the entire air ionization unit.

The invention may also include a controller that (1) measures the amount of particulate in the air, (2) measures the amount of negative and/or positive ions in the air, (3) measures the amount of ozone in the air, (4) measures the amount of carbon monoxide in the air, (5) measures the air temperature and humidity, and/or (6) adjusts the amount of ions being released into the air based on one or more measured parameters.

The contents of this summary section are provided only as a simplified introduction to the disclosure, and are not intended to be used to limit the scope of the appended claims.

BRIEF DESCRIPTION OF THE DRAWINGS

With reference to the following description, appended claims, and accompanying drawings as attached:

DETAILED DESCRIPTION

Figure 1:
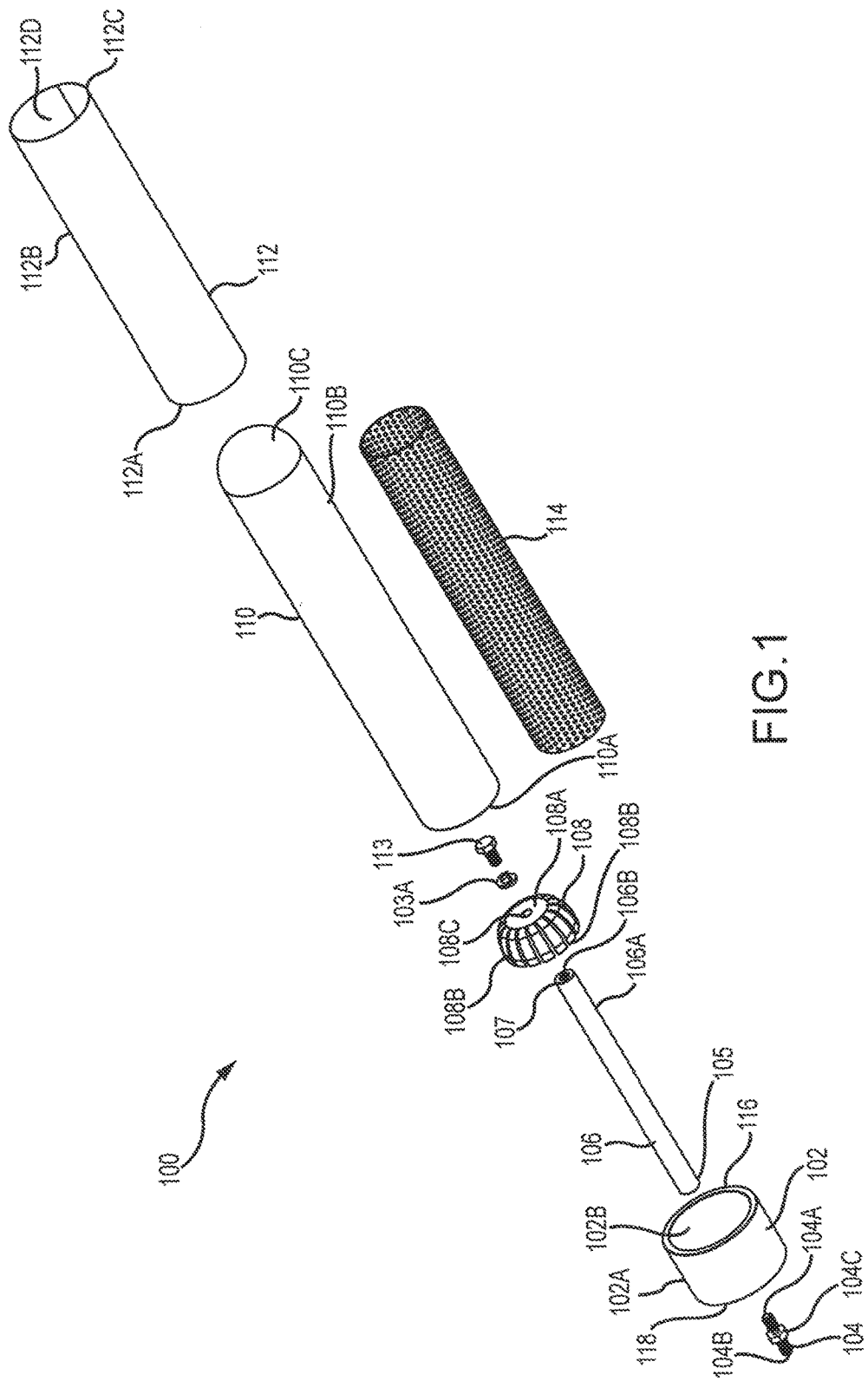
FIG. 1 is an exploded view of an air ionization unit in accordance with embodiments of the invention.
Figure 2:
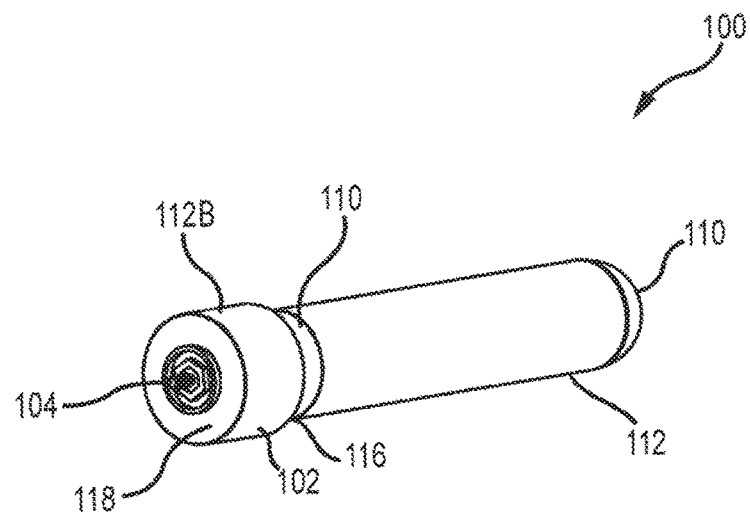
FIG. 2 is an assembled, perspective side view of the air ionization unit of FIG. 1.
Figure 3:
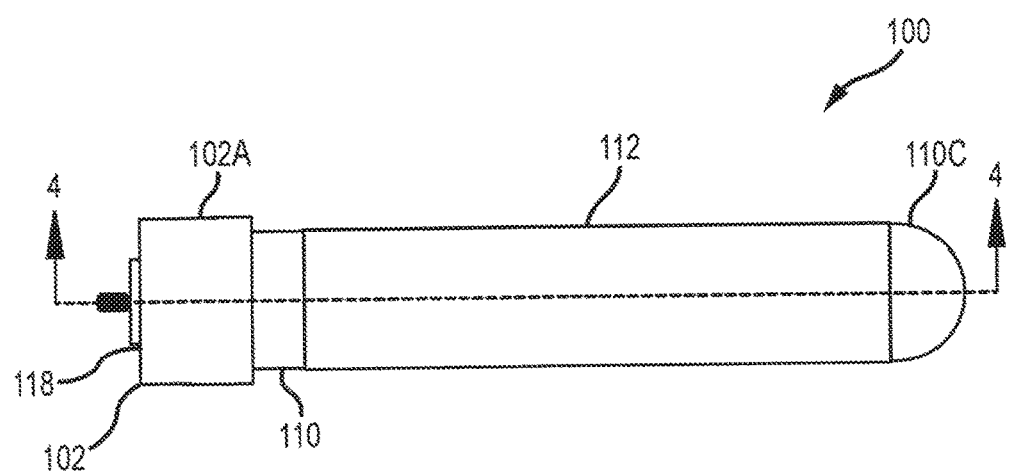
FIG. 3 is an assembled side view of the air ionization unit of FIG. 1.
Figure 4:
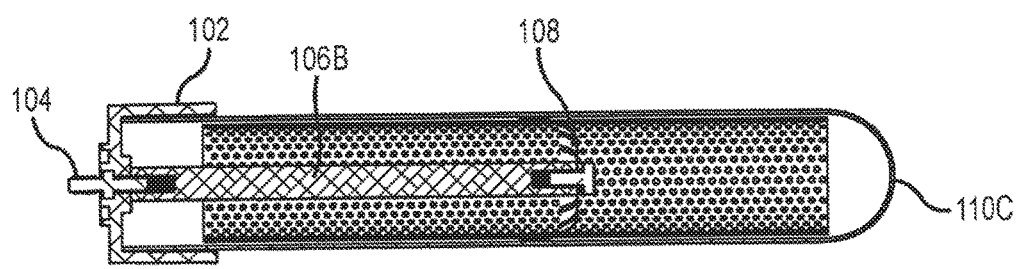
FIG. 4 is a cross-sectional, side view of the air ionization unit of FIG. 3 taken along lines A-A.
Figures 5, 6:
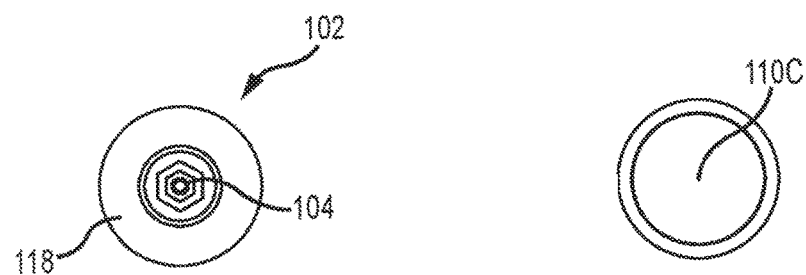
FIG. 5 is an end view of the air ionization unit of FIG. 3.
FIG. 6 is the opposite end view of the air ionization unit of FIG. 3.

The following description is of various exemplary embodiments only, and is not intended to limit the scope, applicability or configuration of the present disclosure in any way. Rather, the following description is intended to provide a convenient illustration for implementing various embodiments including the best mode. As will become apparent, various changes may be made in the function and arrangement of the elements described in these embodiments without departing from the scope of the appended claims.

For the sake of brevity, conventional techniques for ionization, air filtration, ozone removal, and/or the like may not be described in detail herein. Furthermore, the connecting lines shown in various figures contained herein are intended to represent exemplary functional relationships and/or physical couplings between various elements. It should be noted that many alternative or additional functional relationships or physical connections may be present in a practical ionization system or related methods.

Prior approaches to air filtration and/or ionization suffer from various drawbacks. For example, certain air ionization systems, in order to avoid releasing an unacceptable level of ozone, generate ionization levels that are insufficient to fully clean and/or sanitize a particular air stream. Moreover, other air ionization systems have suffered from a lack of configurability and/or intelligent control. Yet other air ionization systems have been complex, expensive, and/or lacking in modular configuration and/or serviceability. These and other drawbacks of prior approaches may remedied by principles of the present disclosure.

Turning now to FIGS. 1 through 6, a module 100 for ionizing air is shown. Module 100 as shown preferably has an end cap or "base" 102, an adapter 104, a coupler 106, an ion dispenser 108, a tube 110, an outer electrode 112, and an inner electrode 114. Base 102 is preferably comprised of any suitable plastic, for example injection-molded ABS (but not ABS-PC) although any suitable material may be used. The purpose of base 102 is to receive coupler 106, ion dispenser 108, and tube 110.

Coupler 106 has a first end 105, a second end 107, an outer surface 106A, and a passageway 106B extending therethrough. In some embodiments, coupler 106 comprises a hollow aluminum rod. Moreover, coupler 106 may comprise a solid bar with an internal thread on each end. Coupler 106 may be configured to conduct electricity.

Adapter 104 as shown is a threaded shaft that bases through an opening (not shown in these Figures) of second end 118 of base 102 and is threadingly received in a passageway 106B at the first end 105 of coupler 106. The opening in second end 118 may also be threaded so as to threadingly receive adapter 104. In the preferred embodiment shown, adapter 104 is a threaded shaft with a first end 104A and a second end 104B. A nut 104C is threadingly received on the threaded shaft, end 105 of coupler 106 is aligned with the opening on the inside of second end 118. First end 104A passes through the opening and is threadingly received in passageway 106B of coupler 106 to retain coupler 106 against second end 118. In some exemplary embodiments, adapter 104 may comprise a solid stainless steel adapter with threaded ends and a central integral hex feature to facilitate rotation thereof.

An ion dispenser (also called an "umbrella shaped conductor") 108 is attached to second end 107 of coupler 106. In various exemplary embodiments, ion dispenser 108 may be configured with an umbrella-like shape. However, ion dispenser 108 may be configured with any suitable shape, as desired. Ion dispenser 108 operates to dispense electricity into inner electrode 114. Ion dispenser 108 as shown in this preferred embodiment is comprised of stainless steel (for example, stainless steel having a thickness of between about 0.006 inches and about 0.015 inches), has a top 108A for attachment to coupler 106, and a plurality of downward extending fingers 108B. In this preferred embodiment, ion dispenser 108 is attached to coupler 106 by aligning an opening in top 108A with passageway 106B at end 107 of coupler 106. Then fastener 113, which as shown is a bolt, is passed through opening 108C and threaded into passageway 106B. A lock washer 113A may be positioned between top 108A and the head of fastener 113.

Inner electrode 114 typically comprises a rolled perforated aluminum sheet, but may comprise any suitable material or combination of materials configured to act as a first electrode for purposes of ionization.

Outer electrode 112 typically comprises a tubular stainless steel wire mesh, for example a 0.008 in diameter Type 316 stainless steel wire mesh configured with a 20×20 per square inch grid. However, outer electrode 112 may comprise any suitable material or combination of materials configured to act as a second electrode for purposes of ionization.

A tube 110 is preferably glass (for example, comprised of borosilicate) and retains coupler 106 and ion dispenser 108. Tube 110 is also operative to insulate inner electrode 114 from outer electrode 112 and thus permit the development of a voltage potential therebetween in order to facilitate ionization. Tube 110 has a first, open end 110A, an outer surface 11013, and a second end 110C. Preferably, after cap 102, coupler 106, and ion dispenser 108 are assembled, inner electrode 114 is placed within tube 110, the first end 110A of tube 110 is positioned over ion dispenser 108 and coupler 106, and is received in cap 102 in a snug to slightly loose fit. Outer electrode 112, which has a first end 112A, an outer surface 1128, a second end 1120, and an inner passage 112D, is positioned over tube 110. In the preferred embodiment shown, outer electrode 112 does not cover second end 110C of tube 110 or extend to cap 102.

In the preferred embodiment, when module 100 is assembled, coupler 106 and ion dispenser 108 are positioned approximately 50-60% inside the length of tube 110. In this manner, electrical current is delivered to approximately the center of inner electrode 114.

Figure 7:
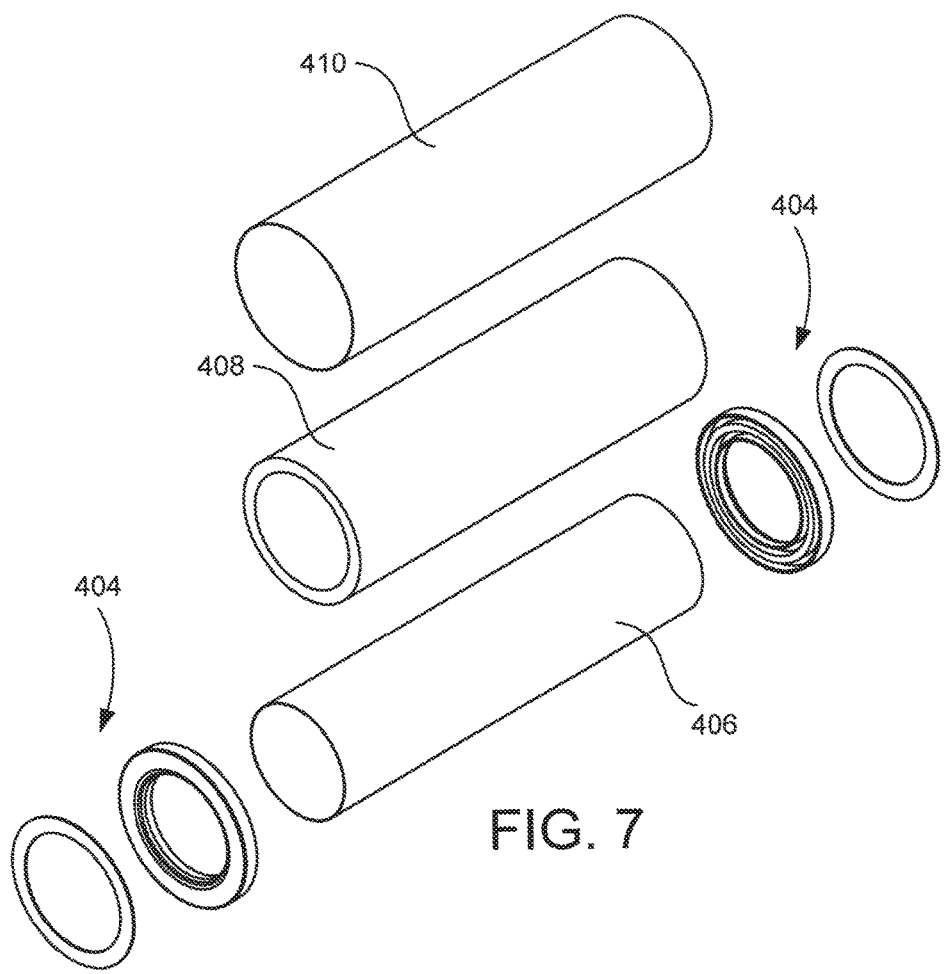
FIG. 7 is an exploded view of an ozone dampening module according to aspects of the invention.
Figure 8:
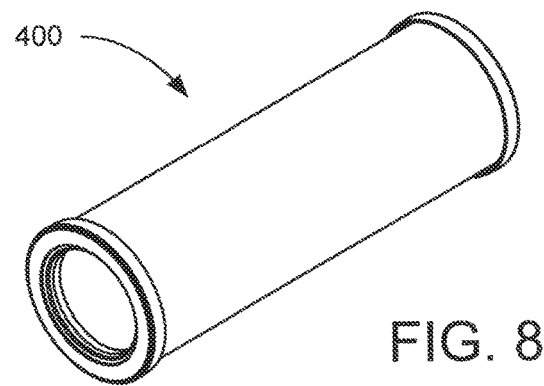
FIG. 8 is a perspective, side view of the assembled ozone dampening module of FIG. 7.
Figure 9:
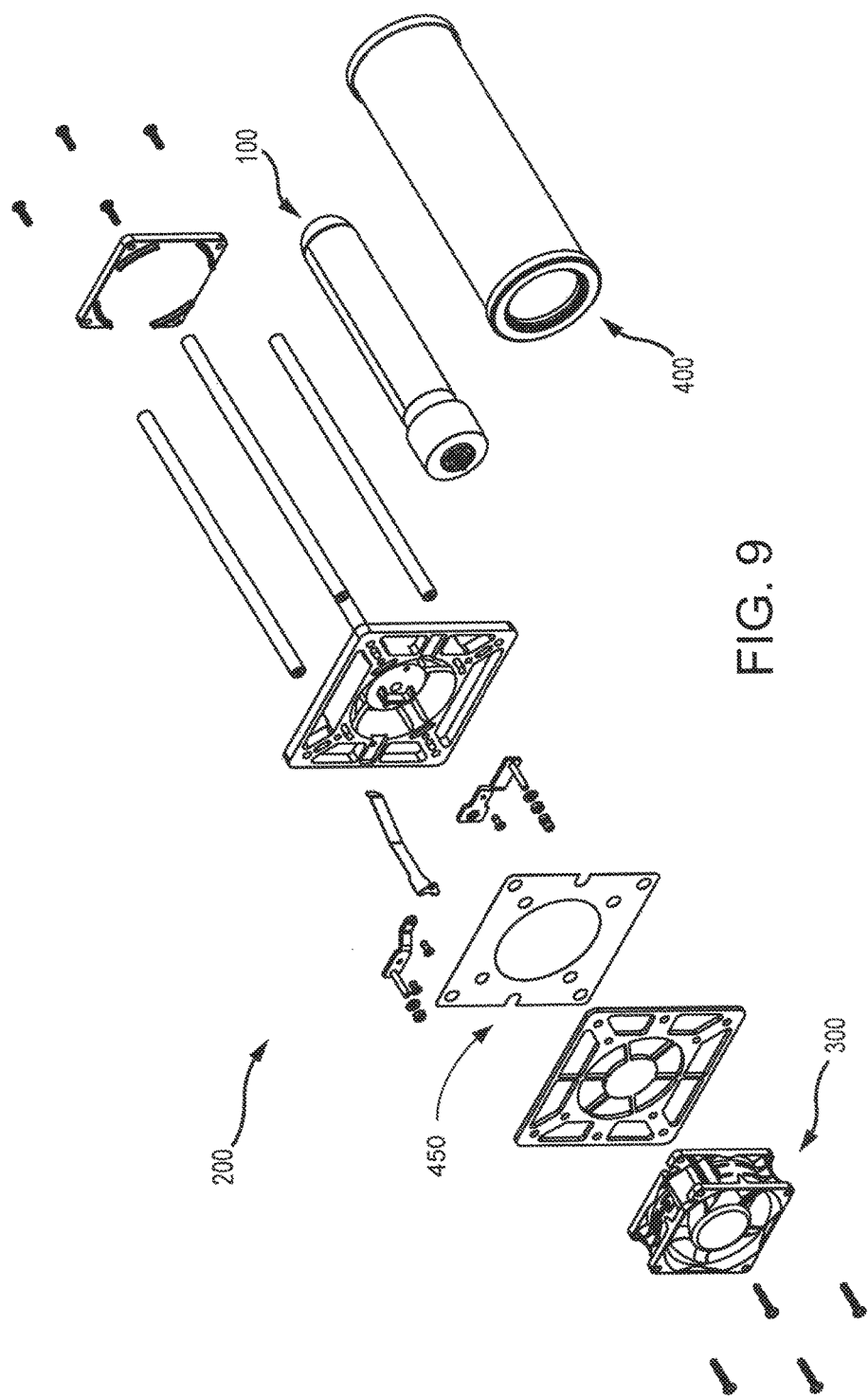
FIG. 9 is an exploded view of an ionization module according to aspects of the invention.
Figure 10:
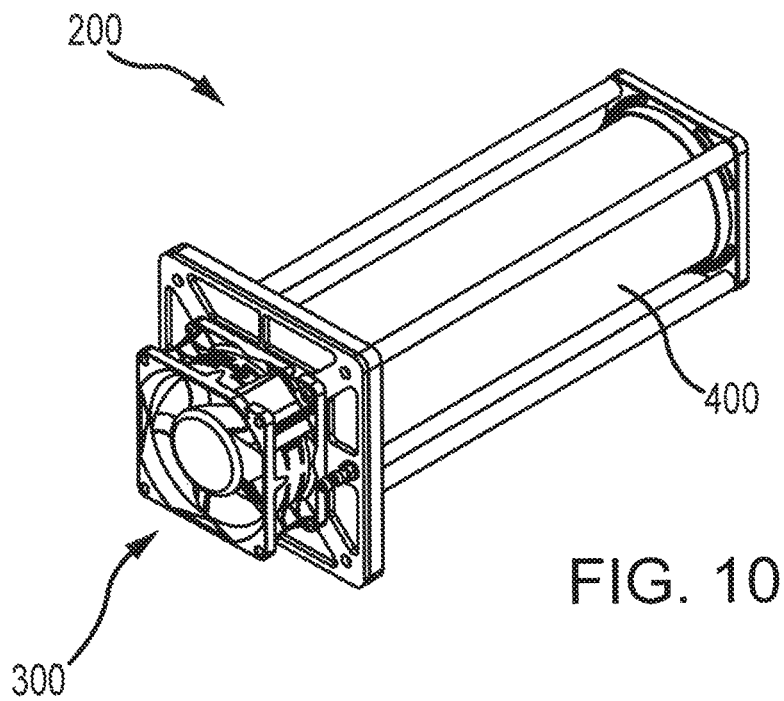
FIG. 10 is an assembled, perspective side view of the ionization module of FIG. 9.
Figure 11:
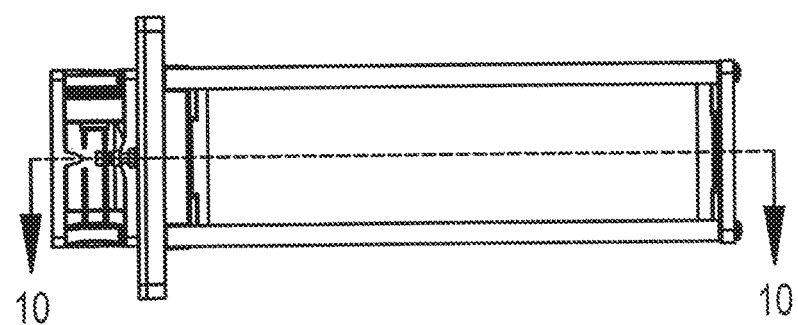
FIG. 11 is an assembled, side view of the ionization module of FIG. 9.
Figure 12:
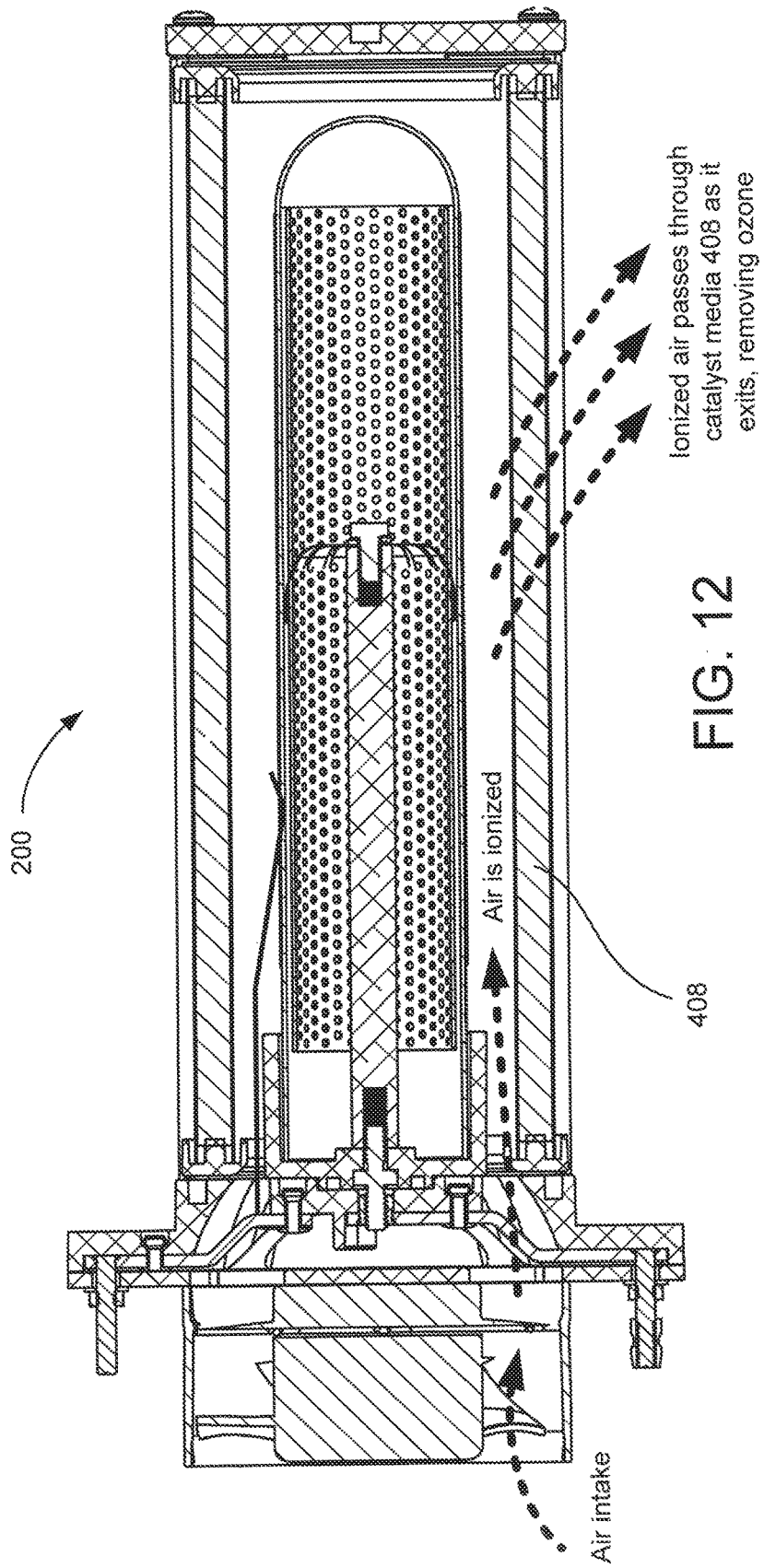
FIG. 12 is a cross-sectional, side view of the ionization module of FIG. 11 taken along lines A-A.
Figure 13:
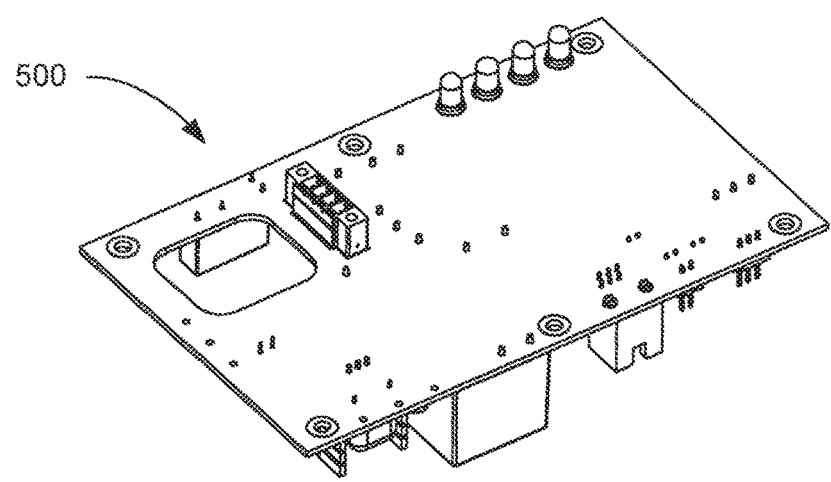
FIG. 13 is a rear, perspective view of a control unit according to aspects of the invention.
Figure 14:
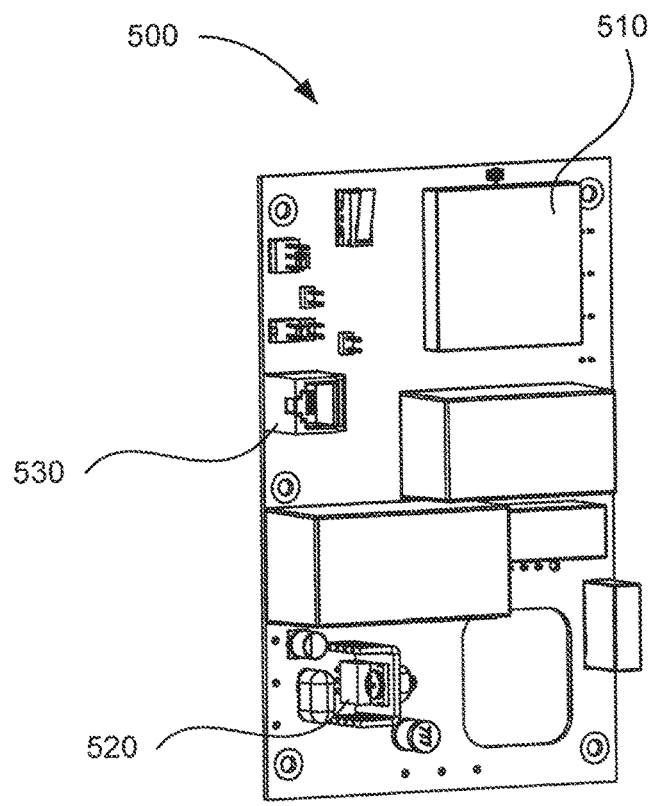
FIG. 14 is a front, perspective view of the control unit of FIG. 13.
Figure 17:
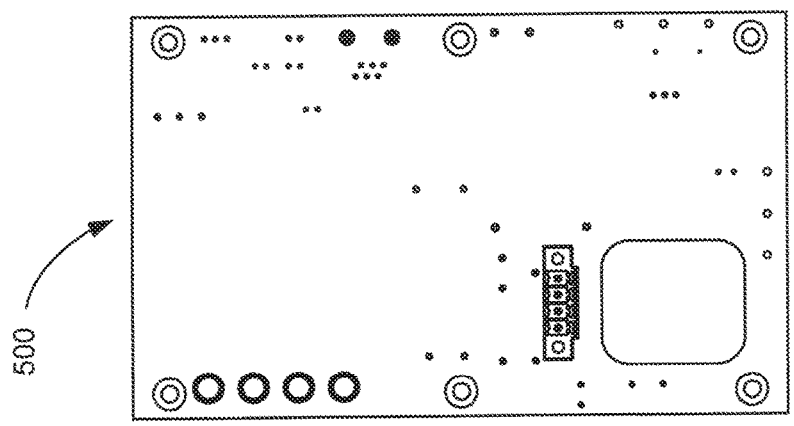
FIG. 17 is a rear view of the control unit of FIG. 13.
Figure 16:
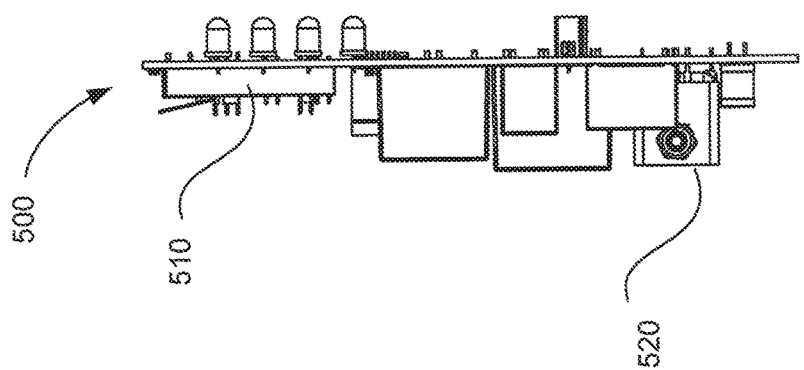
FIG. 16 is a side view of the control unit of FIG. 13.
Figure 15:
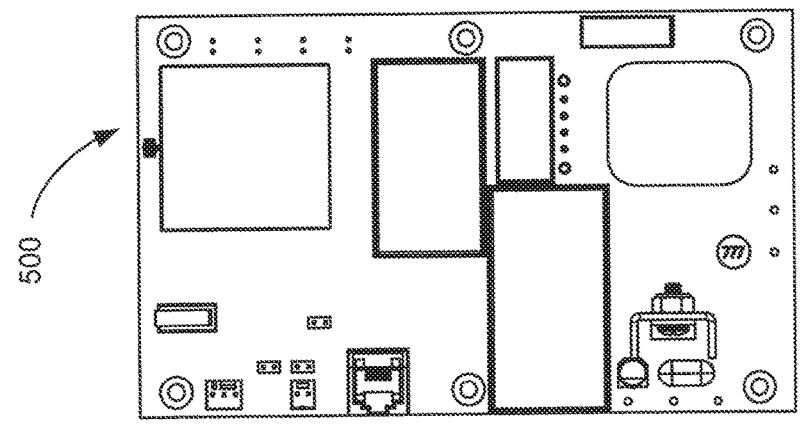
FIG. 15 is a front view of the control unit of FIG. 13.
Figure 18:
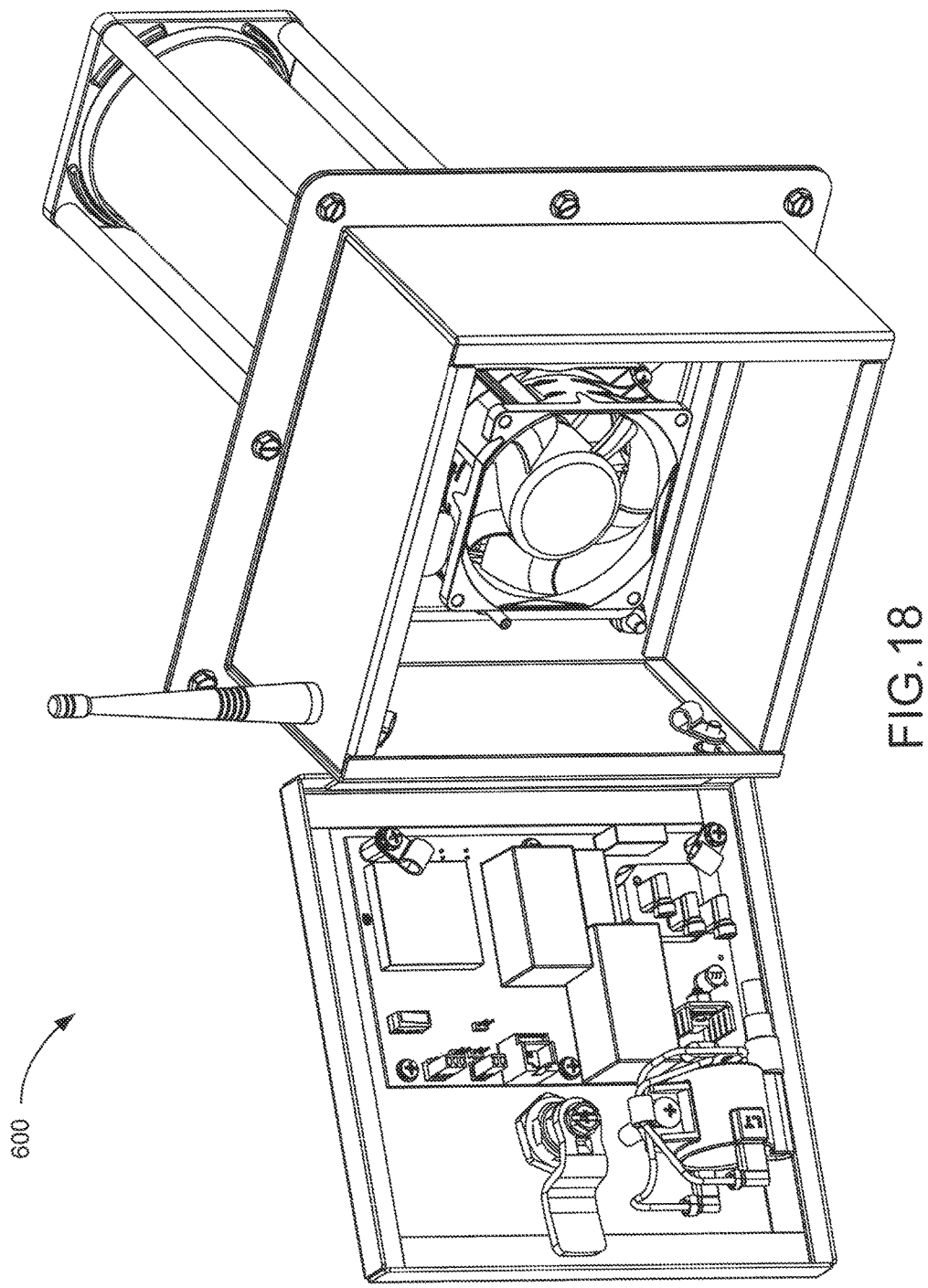
FIG. 18 is a perspective, side view of an ionization system in accordance with aspects of the invention with the housing opened.
Figure 19:
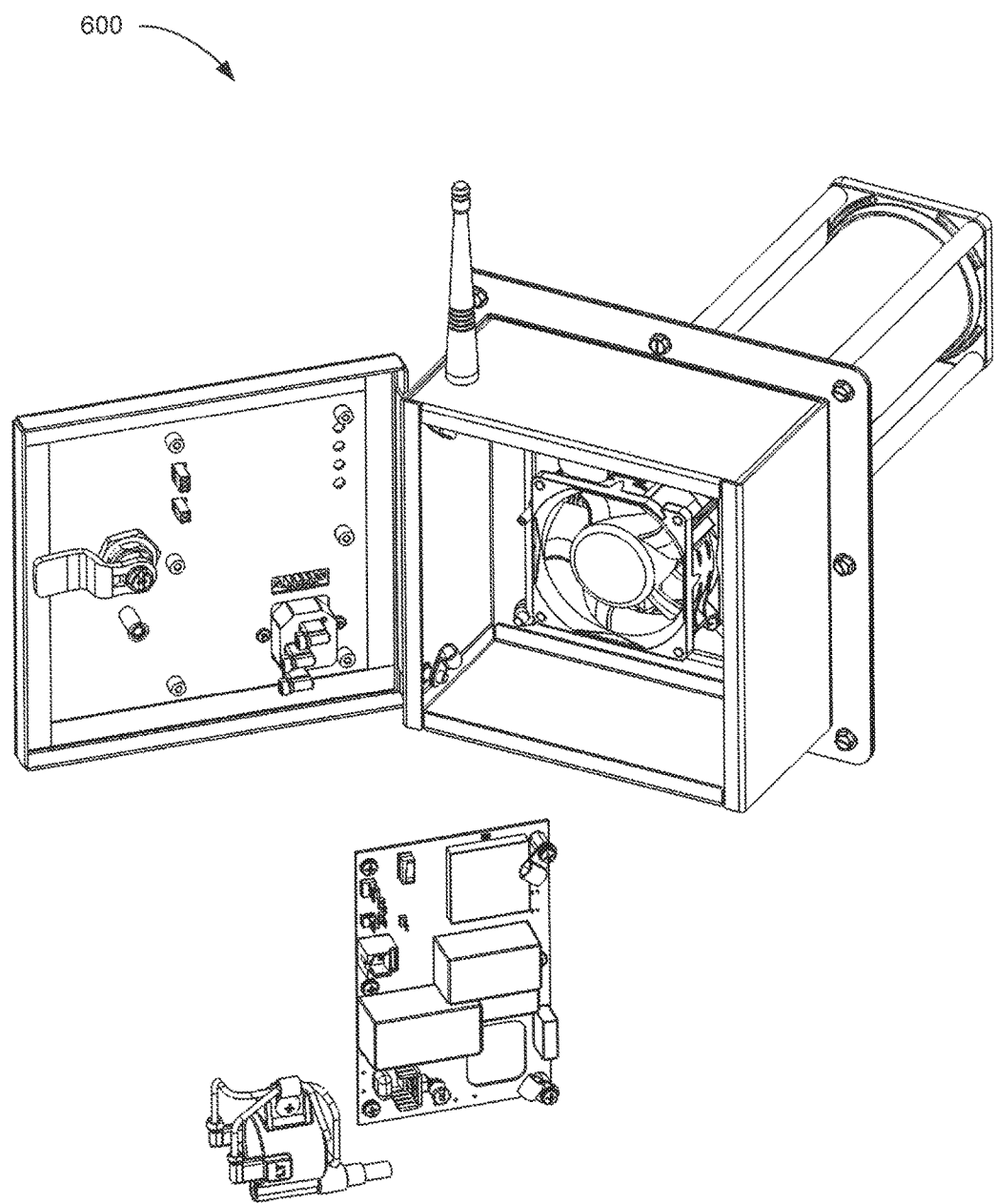
FIG. 19 is a perspective, side view of the ionization system according to FIG. 18 with the control unit and energy converter removed.
Figure 20:
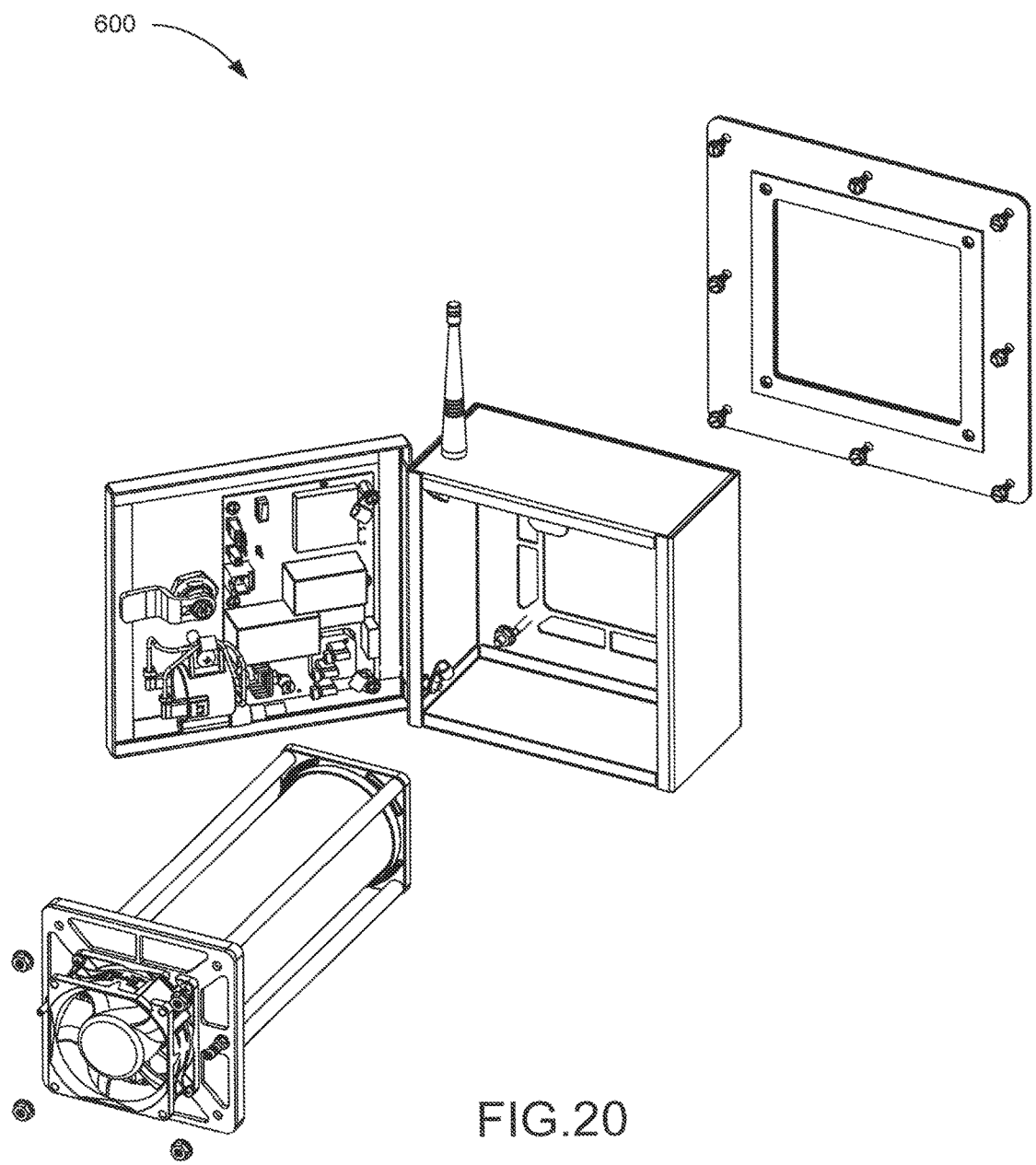
FIG. 20 is a partial exploded view of the ionization system of FIG. 18 showing the ionization module removed from the housing, and the housing removed from a support plate.
Figure 21:
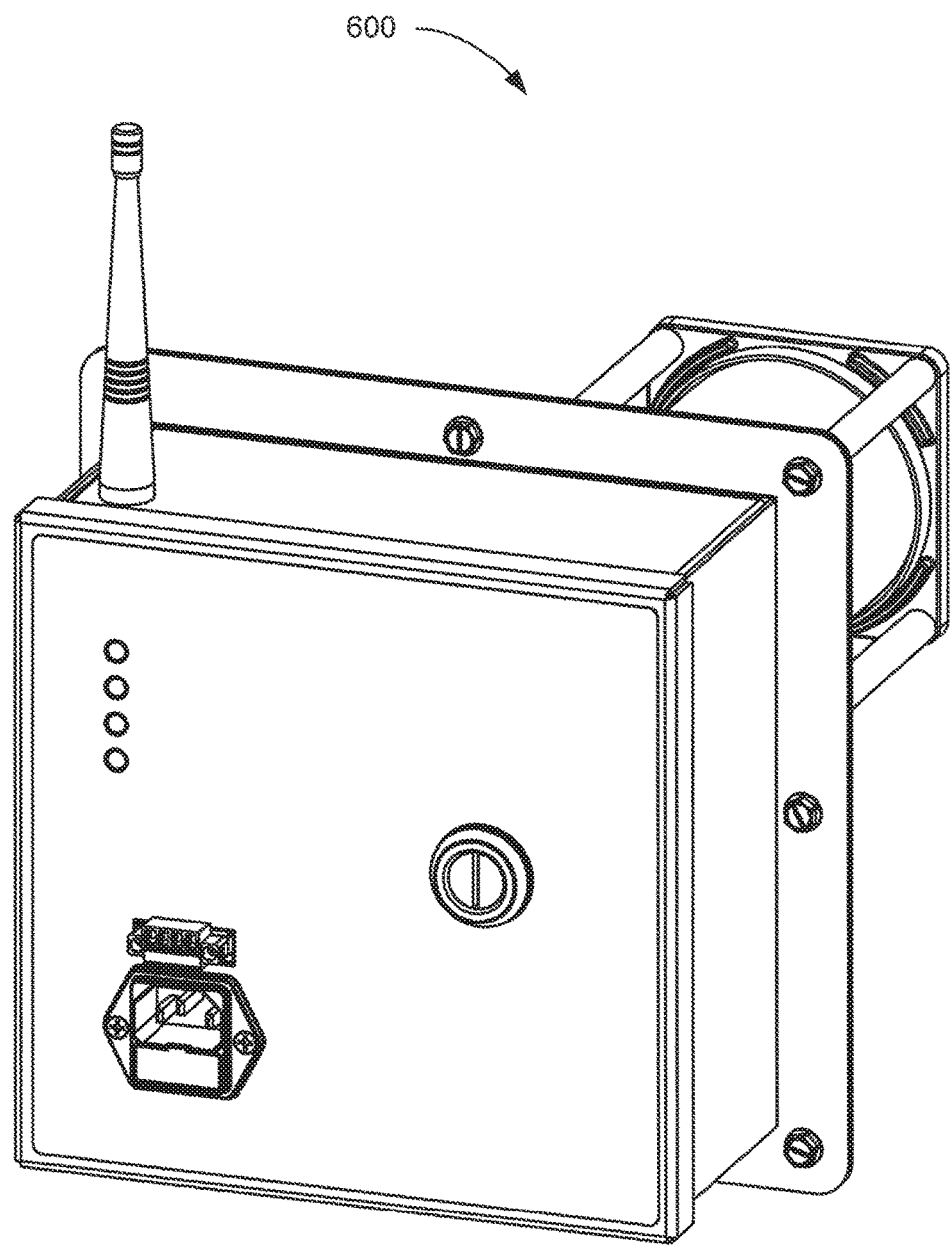
FIG. 21 shows a front, perspective view of an ionization system according to the invention.

With reference now to FIGS. 7 and 8, an ozone removal assembly 400 comprises a tubular inner wall 406, a tubular outer wall 410, and a pair of ends 404. Inner wall 406, outer wall 410, and ends 404 may be coupled together to form a container for a catalyst media 408. In an exemplary embodiment, inner wall 406 and outer wall 410 are coupled to a first end 404 (for example, via MN silicone). First end 404 is disposed on a surface, and the space between inner wall 406 and outer wall 410 is filled with catalyst media 408. Second end 404 is then coupled to inner wall 406 and outer wall 410, securing catalyst media 408 in the resulting assembly. Inner wall 406 and outer wall 410 are configured to be at least partially permeable to air. For example, inner wall 406 and outer wall 410 may comprise rolled stainless steel mesh screen or the like.

In various exemplary embodiments, catalyst media 408 is configured to convert, neutralize, and/or otherwise remove and/or reduce an undesirable compound in the air, for example ozone. Catalyst media 408 may also be referred to as a "catalyst bed", "reaction bed", "ozone destruction catalyst", and/or the like. Catalyst media 408 may be granulated or otherwise shaped or formed to form part of ozone removal assembly 400. Catalyst media 408 typically comprises manganese dioxide, copper oxide, and/or the like, or combinations of the same. In some embodiments, catalyst media 408 comprises Carulite 200 offered by Carus Corporation (Peru, Ill.). However, any suitable catalyst configured to neutralize and/or remove ozone from an airstream may be utilized.

FIGS. 9 through 12 show an ionization and filter cartridge 200 according to a preferred embodiment of the invention. Cartridge 200 includes previously described module 100. It also generally includes a housing and support structure, a fan assembly (or fan) 300, an ozone removal assembly 400, and an air filter 450. Air filter 450 may comprise polypropylene, natural fibers, and/or the like. Air filter 450 is operative to reduce the amount of dust and other airborne particulates entering ozone removal assembly 400, as accumulation of dust on catalyst media 408 reduces its efficacy.

The support structure of cartridge 200 includes a section for supporting module 100 and ozone removal assembly 400, and a section for supporting fan assembly 300, wherein, in the preferred embodiment, when cartridge 200 is fully assembled, it is a single unit that may be removed and replaced when desired.

Turning now to FIGS. 13 through 23, an exemplary ionization and filtration system 600 utilizes module 100 and cartridge 200. System 600 further comprises electronic controls 500. In various exemplary embodiments, electronic controls 500 are configured to control module 100 to generate an ionization level in excess of 66% negative ions; a negative ionization level significantly higher than previous systems. In this manner, module 100 generates a net excess of negative ions, and thus improved air filtration and clearing is achieved. In contrast, prior ionization systems typically generated approximately 50% positive ions and 50% negative ions, thus achieving limited efficacy as many ions quickly recombined and/or neutralized one another and were thus no longer available for air filtration and clearing. In some exemplary embodiments, electronic controls 500 pulse power convertors 520 in a manner suitable to positively bias power convertors 520 with respect to circuit ground; this results in generation of excess negative ions in module 100.

Additionally, electronic controls 500 may further comprise and/or communicate with various inputs (e.g., sensors) which monitor ionization levels, the density of particulates in the air, the ambient humidity, temperature, and/or the like. Based at least in part on the sensor inputs, electronic controls 500 adjust the operation of system 600 to achieve a desired level of filtration, ionization level, and/or the like.

With reference now to FIGS. 13 through 17, electronic controls 500 typically comprise various electronic components; for example: a printed circuit board; RF module 510 for wireless communication via a suitable wireless protocol or protocols (for example; IEEE 802.11 ("WiFi"), IEEE 802.15.4 ("ZigBee"), Bluetooth, GSM, and/or the like); power convertor(s) 520 for creating, modulating, transforming; and/or converting AC and/or DC current, for example for use in operating module 100 to produce ions; wired communication and/or input programming port(s) 530; together with various resistors, capacitors, inductors, transistors, diodes, light-emitting diodes, switches, traces, jumpers, fuses, amplifiers, antennas, and so forth as are known in the art. In various exemplary embodiments, electronic controls 500 further comprise a microprocessor and/or microcontroller (for example, an 8-bit or 16-bit microcontroller, such as the PIC16F1503T-I/SL microcontroller offered by MicroChip Corporation of Chandler, Ariz.). The microcontroller is operative for algorithmic (i.e., pre-programmed) operation, as well as responsive (i.e., pursuant to sensor inputs, communications, etc) operation of system 600.

In one operating mode, electronic controls 500 are configured to operate module 100 at an 80% duty cycle (for example, 4 minutes in an ion generation mode, followed by one minute powered down, followed by 4 minutes in an ion generation mode, and so forth). In another operating mode, electronic controls 500 are configured to operate module 100 at a 100% duty cycle (always on). However, any suitable duty cycle may be utilized.

In various exemplary embodiments, electronic controls 500 are configured to generate up to 6000 volts at frequencies between 1 kHz and 2 kHz for use in ionization. Electronic controls 500 typically draw between about 700 milliamps and about 900 milliamps. Power supplied to module 100 via electronic controls 500 may be digitally managed, for example via a pulse width modulation (PWM) technique utilizing a fixed voltage and variable duty cycle. Moreover, operating parameters for electronic controls 500 may be remotely managed.

In various exemplary embodiments, electronic controls 500 employ a "white noise" mode wherein power convertors 520 are turned on and/or off via randomized timing. In this manner, transformer "whine" or "power line hum" may be reduced and/or eliminated, making the resulting system quieter and/or more suitable for indoor use.

In yet another operating mode, electronic controls 500 are configured to operate system 600 in an "ozone depletion mode" whereby module 100 is powered down and does not create ionization, but air is still passed through catalyst media 408, for example responsive to operation of fan assembly 100 (and/or as a result of ambient airstream movement, for example in an HVAC duct). In this manner, system 600 is operative to remove ozone from the ambient air.

In various exemplary embodiments, electronic controls 500 monitor the performance of module 100 and/or ozone removal assembly 400, and may signal when a component of system 600 needs replacing (for example, due to deterioration of ionization components in module 100, due to dust accumulation on catalyst media 408 in module 400, and/or the like).

Electronic controls 500 are configured to monitor and control various operational characteristics of system 600, for example for safety. In various embodiments, electronic controls 500 monitor fan 300 speed and current draw, as well as module 100 voltage and current draw. System 600 may be shut down and/or restarted if an anomaly is detected. Additionally, electronic controls 500 may monitor status and error conditions, turn an ozone depletion mode on or off, monitor temperature s for operation, and/or adjust a duty cycle associated with operation of module 100.

With reference now to FIGS. 18 through 21, system 600 may be configured to be installed in a ventilation duct, for example an existing HVAC duct of a building. System 600 may be installed in connection with a new build, or as a retrofit.

While various exemplary embodiments of system 600 may be discussed in the context of a residential HVAC installation, it will be appreciated that embodiments of the invention may be deployed in a wide variety of form factors, installation locations, and uses. For example, system 600 may be configured as: a desktop unit for placing on an office desk; a freestanding unit (for example, similar in form factor to a tower-style fan); a unit for installation in a vehicle such as an automobile, bus, or airplane; or a high-volume unit for use in connection with a hospital, school, food processing plant, restaurant, and/or the like. In particular, system 600 may desirably be utilized to sanitize and deodorize air that is exposed to or contains strong-smelling organic contaminants, reducing and/or eliminating undesirable odors.

Figure 22:
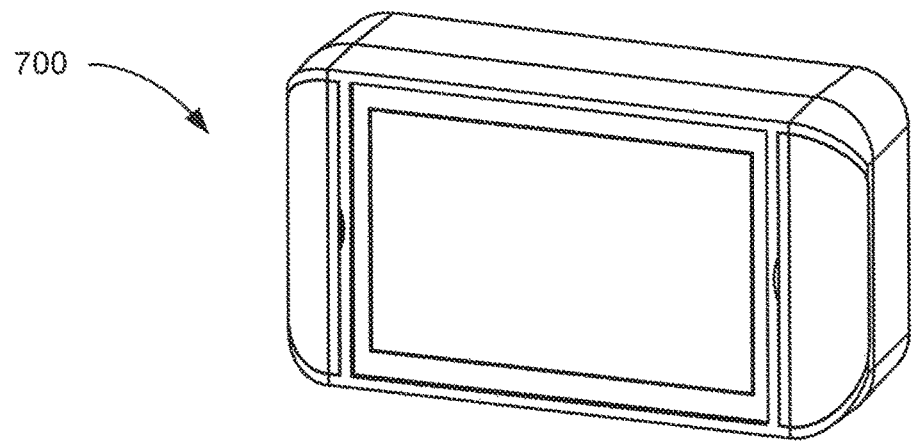
FIG. 22 shows a display that may be used in accordance with aspects of the invention.

In some embodiments, with reference to FIG. 22 system 600 may further comprise a control panel 700. Control panel 700 comprises a display and various inputs, buttons, and the like. Control panel 700 is in wired and/or wireless communication with control electronics 500. Via control panel 700, a user may view statistics regarding operation of system 600, give commands to system 600, view error messages or other system 600 communications, and the like.

Figure 23:
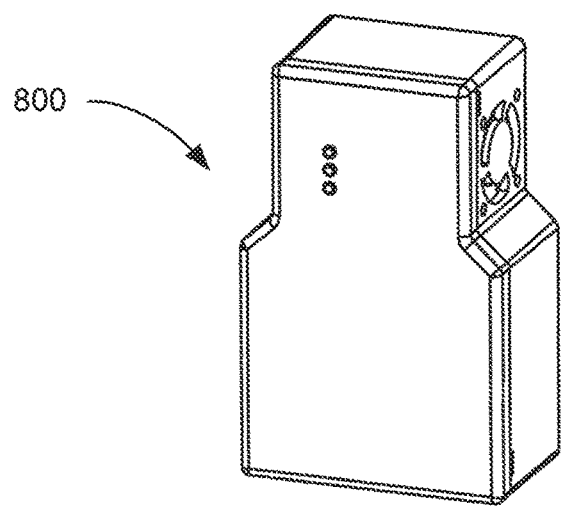
FIG. 23 shows a sensor that may be used in accordance with aspects of the invention.

In various embodiments, with reference to FIG. 23 system 600 may further comprise one or more remote sensors 800. Remote sensor 800 is in wired and/or wireless communication with control electronics 500. Remote sensor 800 comprises various sensors, for example a temperature sensor, particulate sensor, ozone sensor, carbon monoxide sensor, humidity sensor, and/or the like. Responsive to information received from remote sensor 800, control electronics 500 may modify operation of system 600, for example turning module 100 on or off, turning fan 300 on or off, and/or the like. For example, when remote sensor 800 reports ambient ozone above a target threshold, control electronics 500 may operate system 600 in an ozone depletion mode for a period of time until ambient ozone is below a target threshold. Likewise, when remote sensor 800 reports that particulates are above a target threshold, control electronics 500 may increase the duty cycle of module 100 in order to generate increased ionization and thus increase the rate of particulate removal. Remote sensor 800 may be battery powered, or may be configured to be plugged into a power outlet. Multiple sensors 800 may be utilized to provide information regarding an operational environment to control electronics 500.

In various exemplary embodiments, operating parameters for system 600 may be monitored and changed remotely, for example via wireless communication. Changes for system 600 may be supplied via a connected software application operable on a tablet or smartphone, via control panel 700, via a universal serial bus connection to control electronics 500, and/or the like.

While the principles of this disclosure have been shown in various embodiments, many modifications of structure, arrangements, proportions, the elements, materials and components, used in practice, which are particularly adapted for a specific environment and operating requirements may be used without departing from the principles and scope of this disclosure. These and other changes or modifications are intended to be included within the scope of the present disclosure and may be expressed in the following claims.

In the foregoing specification, the invention has been described with reference to various embodiments. However, one of ordinary skill in the art appreciates that various modifications and changes can be made without departing from the scope of the present invention as set forth in the claims below. Accordingly, the specification is to be regarded in an illustrative rather than a restrictive sense, and all such modifications are intended to be included within the scope of the present invention. Likewise, benefits, other advantages, and solutions to problems have been described above with regard to various embodiments. However, benefits, advantages, solutions to problems, and any element(s) that may cause any benefit, advantage, or solution to occur or become more pronounced are not to be construed as a critical, required, or essential feature or element of any or all the claims.

As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. Also, as used herein, the terms "coupled," "coupling," or any other variation thereof, are intended to cover a physical connection, an electrical connection, a magnetic connection, an optical connection, a communicative connection, a functional connection, and/or any other connection. When language similar to "at least one of A, B, or C" or "at least one of A, B, and C" is used in the claims, the phrase is intended to mean any of the following: (1) at least one of A; (2) at least one of B; (3) at least one of C; (4) at least one of A and at least one of B; (5) at least one of B and at least one of C; (6) at least one of A and at least one of C; or (7) at least one of A, at least one of B, and at least one of C. The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

What is claimed is:

1. An air ionization system, comprising:
   (a) an ion generator that generates more negative ions than positive ions;
   (b) an ozone removal assembly containing a catalyst for removal of ozone from the air, wherein the ion generator is disposed at least partially within the ozone removal assembly; and
   (c) a control system that measures an ion count in the air and energizes the ion generator based at least in part on the measured ion count in the air,
   wherein the ion generator comprises:
       a stainless steel ion dispenser configured to receive electrical current responsive to operation of the control system;
       an inner electrode electrically coupled to the ion dispenser, the inner electrode comprising a perforated aluminum sheet;
       a glass tube disposed at least partially around the inner electrode; and
       an outer electrode disposed at least partially around the glass tube, the outer electrode comprising a tubular stainless steel mesh screen.

2. The air ionization system of claim 1 further comprising a fan that forces air into the airspace between the ion generator and the ozone removal assembly.

3. The air ionization of claim 1 further comprising a remote sensor in wireless communication with the control system, wherein the remote sensor measures at least one of an ozone level, an air temperature, a particulate level, a carbon monoxide level, or a humidity, and wherein the remote sensor communicates the measurements to the control system.

4. The air ionization system of claim 1 further comprising a mounting device to couple the air ionization system to an HVAC duct.

5. The air ionization system of claim 1 wherein the control system energizes the ion generator via randomized timing to reduce power line hum.

6. The air ionization system of claim 1, wherein the ozone removal assembly comprises a tubular inner wall, a tubular outer wall, and a space between the tubular inner wall and the tubular outer wall, wherein the catalyst is positioned in the space.

7. The air ionization system of claim 1, wherein the catalyst is granular.

8. The air ionization system of claim 1, wherein the ion generator generates in excess of 66% negative ions.

9. An air ionization system, comprising:
   (a) an ion generator that generates more negative ions than positive ions;
   (b) an ozone removal assembly containing a catalyst for removal of ozone from the air, wherein the ion generator is disposed at least partially within the ozone removal assembly; and
   (c) a control system that measures an ion count in the air and energizes the ion generator based at least in part on the measured ion count in the air;
   wherein the ozone removal assembly comprises:
       an inner stainless steel mesh screen forming a first tube;
       an outer stainless steel mesh screen forming a second tube;
       a pair of end caps coupling the first tube and the second tube; and
       a catalyst media disposed between the first tube and the second tube.

10. The air ionization system of claim 9 further comprising a fan that forces air into the airspace between the ion generator and the ozone removal assembly.

11. The air ionization system of claim 9 further comprising a remote sensor in wireless communication with the control system, wherein the remote sensor measures at least one of an ozone level, an air temperature, a particulate level, a carbon monoxide level, or a humidity, and wherein the remote sensor communicates the measurements to the control system.

12. The air ionization system of claim 9, wherein the catalyst is granular.

13. The air ionization system of claim 9, wherein the ion generator generates in excess of 66% negative ions.

14. An air ionization system, comprising:
(a) an ion generator that generates more negative ions than positive ions;
(b) an ozone removal assembly containing a catalyst for removal of ozone from the air, wherein the ion generator is disposed at least partially within the ozone removal assembly; and
(c) a control system that measures an ion count in the air and energizes the ion generator based at least in part on the measured ion count in the air;
wherein the ion generator is tubular,
wherein the ozone removal assembly is tubular, and
wherein the ion generator is disposed co-axially with, and within, the ozone removal assembly, a cylindrical airspace separating the ion generator from the ozone removal assembly.

15. The air ionization system of claim 14 further comprising a fan that forces air into the airspace between the ion generator and the ozone removal assembly.

16. The air ionization system of claim 14 further comprising a remote sensor in wireless communication with the control system, wherein the remote sensor measures at least one of an ozone level, an air temperature, a particulate level, a carbon monoxide level, or a humidity, and wherein the remote sensor communicates the measurements to the control system.

17. The air ionization system of claim 14 wherein, responsive to operation of a fan, air enters the cylindrical airspace, is negatively ionized responsive to operation of the ion generator, and exits the air ionization system by passing through the catalyst.

18. The air ionization system of claim 14 further comprising an air filter disposed between the fan and the cylindrical airspace.

19. The air ionization system of claim 18 wherein the air filter comprises at least one of polypropylene or cotton.

20. The air ionization system of claim 14, wherein the ozone removal assembly comprises a tubular inner wall, a tubular outer wall, and a space between the tubular inner wall and the tubular outer wall, wherein the catalyst is positioned in the space.

21. The air ionization system of claim 14, wherein the catalyst is granular.

22. The air ionization system of claim 14, wherein the ion generator generates in excess of 66% negative ions.

* * * * *